United States Patent [19]

Farcilli et al.

[11] 4,291,038

[45] Sep. 22, 1981

[54] CEREBRAL VASODILATING 20,21-DINOREBURNAMENINE DERIVATIVES

[75] Inventors: Andre Farcilli, Rosny-sous-Bois; Italo Medici, Bondy; Robert Fournex, Paris, all of France; Fernando Barzaghi, Monza, Italy

[73] Assignee: Roussel Uclaf, Romainville, France

[21] Appl. No.: 137,913

[22] Filed: Apr. 7, 1980

Related U.S. Application Data

[63] Continuation of Ser. No. 879,387, Feb. 21, 1978, abandoned.

[30] Foreign Application Priority Data

Feb. 22, 1977 [FR] France ............................... 77 05067

[51] Int. Cl.³ ................. A61K 31/445; C07D 461/00
[52] U.S. Cl. .................................. 424/256; 546/51
[58] Field of Search ........................... 546/51; 424/256

[56] References Cited

U.S. PATENT DOCUMENTS 3,542,796 11/1970 Schut ................................... 546/51
3,755,335 8/1973 Thal et al. ........................... 546/51

FOREIGN PATENT DOCUMENTS 1586697 2/1970 France ................................. 546/51
1440634 6/1976 United Kingdom ................. 546/51

OTHER PUBLICATIONS

Aurousseau, M., *Eur. J. Med. Chem.-Chim. Ther.*, 6, 221–234 (1971).

*Primary Examiner*—Richard A. Schwartz
*Attorney, Agent, or Firm*—Bacon & Thomas

[57] ABSTRACT

New 20,21-dinoreburnamenine derivatives are disclosed which have the formula I

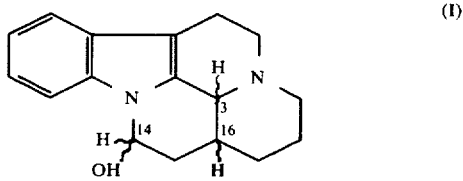

wherein the hydroxyl in the 14-position of the molecule is in either of the two possible positions at the carbon atom in the 14-position to which the isomers A and B correspond and the hydrogens in the 3-position and the 16-position of the molecule are in cis- or in trans-position to each other, and their pharmaceutically acceptable acid addition salts, as well as pharmaceutical formulations thereof.

The new compounds of formula I are prepared by reducing the corresponding 14-oxoderivatives. They are effective in favorably influencing the cerebral vascular circulation.

16 Claims, No Drawings

CEREBRAL VASODILATING 20,21-DINOREBURNAMENINE DERIVATIVES

This is a continuation of application Ser. No. 879,387, filed Feb. 21, 1978, now abandoned.

BACKGROUND OF THE INVENTION

The present invention relates to new 20,21-dinoreburnamenine derivatives, that is eburnamenine derivatives which unlike other eburnamenine derivatives do not contain an ethyl substituent (comprising the $C_{20}$ and $C_{21}$ atoms of the eburnamenine structure) attached to the heterocyclic structure, a process for their preparation and pharmaceutical composition thereof.

Eburnamine, a 14,15-dihydroeburnamenine-14-ol is a secondary alkaloid of the australian plant Hunteria eburnea Pichon (see, e.g., F. Bartlett et al, Compt. Rend. 240,1 (1955). A semisynthetic optical antipod of eburnamine, which exhibits vasodilatory properties is disclosed in the French Pat. No. 15 86 697.

SUMMARY OF THE INVENTION

It is an object of the present invention to provide new pharmacologically-active 20,21-dinoreburnamenine derivatives which are effective in favorably influencing cerebral vascular circulation and ameliorating the oxygen-supply in the brain.

It is a further object of the present invention to provide such new compounds which are effective in preventing and/or ameliorating health disorders which are connected with disturbances of the vascular circulation in the brain and/or cerebral vascular deficiencies.

In order to accomplish the foregoing objects according to the present invention there are provided new compounds having the formula I

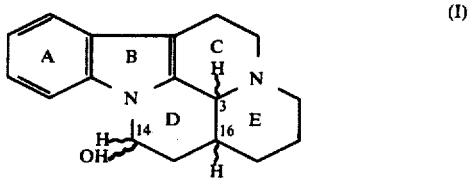

(I)

wherein the hydroxyl in the 14-position of the molecule is in either of the two possible positions at the carbon atom in the 14-position to which the isomers A and B correspond and the hydrogens in the 3-position and the 16-position of the molecule are in cis- or in trans-position to each other, racemates and mixtures thereof, and pharmaceutically acceptable acid addition salts thereof.

According to the present invention, there are further provided processes for preparing the compounds of formula I. The compounds of formula I are prepared by a process which comprises the step of reducing a compound of formula II

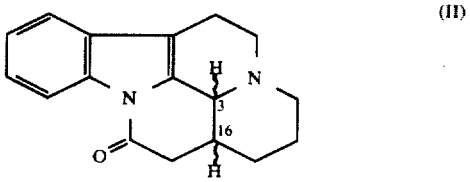

(II)

into a compound of formula I whereby a reduction product is obtained which is the isomer A of the compound of formula I, the isomer B of the compound of formula I or a mixture thereof. The reduction is preferably effected by means of a mixed metal hydride. The amounts of isomers A and/or B in the reduction product vary depending on the alkalinity of the reaction medium. Isomer B or mixtures of isomers A and B can be converted into isomers A by treatment with an alkaline agent.

The new compounds of formula I exhibit valuable pharmacological properties and are in particular effective in ameliorating the cerebral vascular circulation.

According to the present invention there are further provided pharmaceutical compositions comprising the above described compounds of formula I and their pharmaceutically-acceptable acid addition salts and an inert diluent.

Further objects, features, and advantages of the present invention will become apparent from the detailed description of the invention which follows:

DETAILED DESCRIPTION OF THE INVENTION

Within the compounds of formula I, the hydroxyl and the hydrogen in the 14-position of the molecule each can take either of the two possible positions around the carbon atom to which they are connected. Thus, two isomeric forms of the compounds of formula I exist, corresponding to the two possible positions of the hydroxyl in the 14-position. Within the present specification and claims, these isomers are designated as isomers A and B. The compounds of formula I according to the present invention comprise the optically active and the racemic forms of these compounds.

Within the compounds of formula I, the hydrogen atom in the 3-position and the hydrogen atom in the 16-position can each be either in α- or in β-position to the plan of the molecule. Thus, the compounds of formula I comprise two diastereoisomeric groups of compounds, namely compounds of formula I wherein the fusion of the rings D and E is either cis or trans.

The physical data of an isomer A of the compound of formula I wherein the hydrogen atom in the 3-position and the hydrogen atom in the 16-position are in cis-position to each other are given below.

This isomer A exhibits a certain configuration at the carbon atom in 14-position.

The compounds of formula I, either in their optically active form or their racemic form and the salts thereof, wherein the hydrogen atom in the 3-position and the hydrogen atom in the 16-position are in cis-position to each other and wherein the configuration at the carbon atom in the 14-position is the same as the above isomer A, equally are designated as "isomers A".

The epimers of the foregoing products, wherein the positions of the hydroxyl and the hydrogen at the carbon atom in the 14-position are reversed are designated as "isomers B".

The physical data of an isomer A and of an isomer B of a compound of formula I wherein the hydrogen atom in the 3-position and the hydrogen atom in the 16-position are in trans-position to each other are given further below.

The isomer A exhibits a certain configuration at the carbon atom in the 14-position.

The compounds of formula I, either in their optically active form or their racemic form and the salts thereof, wherein the hydrogen atom in the 3-position and the hydrogen atom in the 16-position are in trans-position to each other which exhibit the same configuration at the carbon atom in the 14-position as the above isomer A are designated as "isomers A".

Likewise, the epimers of the latter products wherein the positions of the hydroxyl and the hydrogen at the carbon atom in the 14-position are reversed are designated as "isomers B".

From the foregoing it follows, that the term "isomer A" applies to different compounds wherein, as the case may be, the absolute configuration at the carbon atom in the 14-position is not always the same.

The scope of the present invention, of course, also includes mixtures of different isomers of the compounds of formula I, in particular mixtures of the epimers A and B of a compound of formula I.

In the context of the present specification, the term "mixtures" is meant to denote mixtures which contain the various isomers in any desired portions.

The pharmacologically-acceptable acid addition salts of the compounds of formula I comprise addition salts of pharmacologically-acceptable mineral and organic acids. Examples of suitable acids are hydrochloric acid, hydrobromic acid, hydrogeniodide, nitric acid, sulfuric acid, phosphoric acid, acetic acid, formic acid, benzoic acid, maleic acid, fumaric acid, succinic acid, tartaric acid, citric acid, oxalic acid, glyxolic acid, aspartic acid, ascorbic acid, alkyl monosulfonic acids, such as methane sulfonic acid, ethane sulfonic acid, propane sulfonic acid, alkyl disulfonic acids, such as methane disulfonic acid, α,β-ethane disulfonic acid, aryl monosulfonic acids, such as benzene sulfonic acid, and aryl disulfonic acids.

According to an embodiment of the present invention, the hydrogen atom in the 3-position and the hydrogen atom in the 16-position of the compounds of formula I are in trans-position to each other.

According to another embodiment of the present invention, the hydrogen atom in the 3-position and the hydrogen atom in the 16-position of the compounds of formula I are in cis-position to each other.

Amongst the compounds according to the present invention, the following are cited in particular:
the isomer A of (±) 14,15-dihydro-(3α,16α)-20,21-dinoreburnamenine-14-ol this isomer A is characterized by the following physical data:
¹H NMR-spectrum in deuteropyridine chemical shift of the hydrogen in the 14-position δ=5.90 ppm±0.1 ppm the isomer A of (±) 14,15-dihydro-(3β,16α)-20,21-dinoreburnamenine-14-ol this isomer is characterized by the following physical data:
¹H NMR-spectrum in deuteropyridine chemical shift of the hydrogen in the 14-position δ=6.26 ppm±0.1 ppm
the isomer B of (±) 14,15-dihydro-(3β,16α)20,21-dinoreburnamenine-14-ol this isomer is characterized by the following physical data:
¹H NMR-spectrum in deuteropyridine chemical shift of the hydrogen in position 14 δ=5.76 ppm±0.1 ppm (The various above cited δ-values may vary slightly depending on the acidity of the medium).

According to the present invention, the compounds of formula I in their optically active or racemic form and acid addition salts thereof with organic or inorganic acids are prepared in a process which comprises the step of treating a compound of formula II

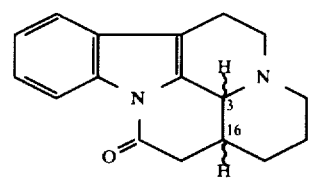

with a reducing agent, whereby the epimer A, the epimer B, or a mixture thereof is obtained. If desired, the resulting product is further transformed into a salt by treating it with an inorganic or an organic acid.

By reducing a compound of formula II, a reduction product is obtained wherein either substantially only one of the isomers A and B of a corresponding compound of formula I or a mixture of the two isomers A and B is present wherein the ratio between the two isomers can vary largely. The amount of the isomer A in the reduction product is depending on the reaction conditions, in particular the alkalinity of the reaction medium. The amount of the isomer A in the reaction product is the more increased, the more strongly alkaline the reaction medium is.

The starting compounds of the formula II can be used in either their optically active or their racemic form.

The products of formula I which are obtained from a product of formula II of course possess the corresponding stereochemical structure.

The compounds of formula II can be used in the form of acid addition salts thereof with mineral or organic acids. In this case the reduced products of formula I can be obtained either in salt form or as a free base, depending on the chosen reaction conditions.

According to a prefered embodiment of the invention the above described process is carried out as follows:
A hydride, preferably a mixed hydride is used as reducing agent. Examples of suitable reducing agents are lithium-aluminum-hydride, sodium-aluminum-diethyl hydride.
The reduction is carried out in the presence of at least one organic solvent or a mixture of solvents. Suitable solvents are, for example, ethers, such as diethyl ether or tetrahydrofurane, aromatic hydrocarbons, such as toluene, benzene or xylene.
The reduction is performed at a temperature of between about −20° C. and the boiling temperature of the reaction mixture. Advantageously the reaction takes place at about room temperature.
In the event that a metal hydride is used as the reducing agent, the compound of formula I is liberated from the intermediary hydride complex in a conventional manner by adding an alkaline aqueous solution, such as for example a sodium hydroxide solution to the reaction mixture.
If a mixture of epimers A and B is obtained, either of the two epimers A or B or both of them can be isolated from the mixture.

If desired, the separate isomers can subsequently be converted into a salt by treating them with an acid.

Likewise, the mixture of the epimers A and B can be treated with an acid and the resulting salts subsequently be separated or one of the resulting salts of the epimers A or B be isolated from the salt mixture.

The recovery of one of the epimers A or B from the mixture thereof can be carried out by conventional methods, such as chromatography, direct crystallization, differential dissolution, e.g., differential dissolution in toluene with heating.

According to an embodiment of the present invention an isomer A of a compound of formula I can also be prepared by treating the isomer B of the compound of formula I or a mixture of the epimers A and B of the compound of formula I with an alkaline agent.

Preferably the process according to this embodiment is carried out in the following way:

The alkaline agent which is used suitably is an alkali-metal hydroxide, such as, e.g., sodium hydroxide, potassium hydroxide, or lithium hydroxide. It can also be, for example, ammonium hydroxide or barium hydroxide.

The reaction is carried out in the presence of a solvent such as an alcohol (for example methanol or ethanol).

Furthermore, the above defined optically active forms of the compounds of formula I can be prepared by splitting the racemates according to conventional methods which are known in the art.

The compounds of formula I as defined above and their pharmacologically-acceptable acid addition salts with mineral or organic acids, exhibit valuable pharmacological properties. In particular they are highly valuable cerebral oxygen generators and vasoregulators. In particular they are effective in increasing the cerebral flow at the level of the cerebral microcirculation.

Due to these pharmacological properties, the compounds of formula I as defined above, in optically active or racemic form, as well as their acid addition salts with pharmaceutically-acceptable mineral or organic acids, are useful as therapeutical agents in the medical art.

Among the therapeutically active agents, the following are cited:

compounds of the above defined formula I wherein the hydrogen atom in the 3-position and the hydrogen atom in the 16-position are in trans-position to each other compounds of the above defined formula I wherein the hydrogen atom in the 3-position and the hydrogen atom in the 16-position are in cis-position to each other, and in particular the isomer A of the ($\pm$) 14,15-dihydro-($3\alpha,16\alpha$)-20,21-dinoreburnamenine-14-ol the isomer of A of the ($\pm$) 14,15-dihydro-($3\beta,16\alpha$)-20,21-dinoreburnamenine-14-ol the isomer B of the ($\pm$) 14,15-dihydro-($3\beta,16\alpha$)-20,21-dinoreburnamenine-14-ol.

All the above defined compounds are pharmacologically-active agents which are very useful in human therapy for treating and/or preventing cerebral vascular disorders and diseases and health disorders which ar provoked by a change in the cerebral circulation. They are useful in preventing and/or diminishing the effects of cerebral arteriosclerosis, cerebral circulation disorders and cerebral or meningital hemorrhages. In particular they can be used in the treatment of cerebral insufficiencies, cerebro-vascular irregularities and injuries and cranial traumatism.

According to the present invention there are further provided pharmaceutical compositions which comprise at least one compound of the formula I as defined above or a pharmaceutically-acceptable acid addition salt thereof. These pharmaceutical compositions may be adapted for the digestive or parenteral administration. They may take the form of solid or liquid formulations which are commonly used in human medicine, such as, for example, tablets, coated tablets, capsules, granulates, suppositories, and injectable solutions. These compositions are prepared according to conventional methods.

Within these compositions, the pharmacologically-active agents may be incorporated into carrier materials which are conventionally used in pharmaceutical compositions, such as talcum, gum arabic, lactose, starch, magnesium stearate, cocoa butter, aqueous or nonaqueous vehicles, vegetable or animal oils and fats, paraffin derivatives, glycols, various wetting agents, dispersing agents, emulsifying agents, and preservatives.

The administered dose of the pharmacologically-active agent varies depending on the type of the compound which is used, the person and the condition which are treated, for example, the usual dose for an adult person can vary from about 10 to about 200 mg orally applied daily.

The compounds of formula II, in optically active or racemic form, and a process for preparing same, are known in the art. For example, the compounds of formula II can be prepared according to the methods which are disclosed in the French Pat. No. 2 190 113 and the Belgian Pat. No. 764 166.

The following examples further illustrate the present invention, yet are non-limiting.

EXAMPLE 1: Isomer A of ($\pm$) 14,15-dihydro-($3\alpha,16\alpha$)-20,21-dinoreburnamenine-14-ol 22 g of ($\pm$)-($3\alpha,16\alpha$)-20,21-dinoreburnamenine-14(15H)-one are dissolved in 220 ml of anhydrous toluene under agitation at a temperature of 18° C. and under nitrogen atmosphere. Whilst maintaining the temperature at 18° C.±1° C., 205 ml of a solution containing 25 g of sodium aluminum diethyl hydride per 100 g of toluene are added within a period of 20 minutes and the mixture is maintained under agitation at the same temperature for a further period of 30 minutes. Subsequently, 205 ml of an aqueous 5 N sodium hydroxide solution are added within a period of 40 minutes, whereby the temperature of the mixture is retained at about −10° C. The mixture is further agitated for 1 hour at a temperature of 25° C., and then the resulting raw product is filtered off, washed two times with 300 ml of water each, and dried. 20.4 g of the raw product are thus obtained.

The raw product is re-dissolved in a mixture of 250 ml methylene chloride and 100 ml of methanol, the solution is treated with active charcoal, the charcoal is centrifuged off and washed with the mixture of methylene chloride-methanol (50-20), the solution is then evaporated to dryness, 60 ml of methylene chloride are added to the residue and the mixture is again evaporated to dryness, the residue is then again mixed with 60 ml of methylene chloride under stirring at 25° C. for a period of 10 minutes. After the resulting paste is centrifuged, washed with methylene chloride, and dried, 18.22 g of the product are obtained. 18 g thereof are recrystallized in methanol, whereby 17 g of the product are obtained, 16.5 g of which are once more purified. These 16.5 g of the product are introduced into 100 ml of demineralized water, 200 ml of a 1 N-hydrochloric acid are added, then 102 ml of a 2 N-sodium hydroxide solution are added, the mixture is further agitated during a period of 30 minutes at room temperature, centrifuged, the residue washed with 2 l of water and dried in a ventilated oven at a temperature of between 70° and 80° C. 14.7 g of the final product are obtained.

PHYSICAL DATA OF THE PRODUCT

Melting point: 230° C.

Elementary analysis: $C_{17}H_{20}N_2O$. calculated 76.08% C, 7.51% H, 10.44% N. found 75.8% C, 7.4% H, 10.2% N.

UV-spectrum (in 0.1 N—HCl/ethanol)

maximum at 223 nm ($\epsilon = 36,000$)
maximum at 272 nm ($\epsilon = 8,050$)
maximum at 279 nm ($\epsilon = 7,500$)
maximum at 290 nm ($\epsilon = 5,500$).

NMR-spectrum (in deuteropyridine): absorption at 1.90 ppm: hydrogen in the 14-position.

EXAMPLE 2: Isomer A of (±)14,15-dihydro-(3β,16α)-20,21-dinoreburnamenine-14-ol 30 g of (±)(3β,16α)-20,21-dinoreburnamenine-14(15H)one hydrochloride are suspended in 300 ml of anhydrous toluene at a temperature of 20° C. Whilst maintaining the temperature at 20°-22° C., 300 ml of a solution containing 25 g of sodium aluminum diethyl hydride per 100 g of toluene are added within a period of 30 minutes, then 300 ml of an aqueous 5 N sodium hydroxide solution are added very slowly, whilst always maintaining the mixture at the same temperature. Then the mixture is agitated for another 30 minutes and is extracted with about 4 l of a mixture of methylene chloride-methanol 1:1, and the extract is washed with water, dried and evaporated to dryness under vacuum. The residue is purified several times by mixing it with methanol and 23.2 g of the product are obtained. 22.9 g of this product are introduced into 230 ml of demineralized water, 200 ml of a 1 N hydrochloric acid solution are added, filtered, the filter rinsed with water, and then 100 ml of 1 N sodium hydroxide solution are added to the solution under agitation, the mixture is further agitated for 30 minutes, centrifuged, and the residue is washed with water and dried. 22.5 g of the final product are obtained.

PHYSICAL DATA OF THE PRODUCT

Melting point: 252° C.

Elementary analysis: $C_{17}H_{20}ON_2$ calculated 76.08% C, 7.51% H, 10.44% N. found 76.1% C, 7.6% H, 10.2% N.

UV-spectrum (in 0.1 N-HCl-ethanol)

maximum at 223 nm ($\epsilon = 36,000$)
maximum at 270 nm ($\epsilon = 8,000$)
maximum at 278 nm
maximum at 289 nm ($\epsilon = 4,700$)

NMR-spectrum (in deuteropyridine):

absorption at about 6.26 ppm: hydrogen in the 14-position aromatics: massive centered at about 7.41 ppm.

EXAMPLE 3: Isomer A of the (±)14,15-dihydro-(3β,16α)-20,21-dinoreburnamenine-14-ol STAGE A mixtures of the two epimers A and B of the (±)14,15-dihydro-(3β,16α)-20,21-dinoreburnamenine-14-ol 74.8 g of (±)(3β,16α)-20,21-dinoreburnamenine-14(15H)-one are dissolved in 748 ml of toluene under an inert gas atmosphere. 140.6 ml of a solution containing 25 g of sodium aluminum diethyl hydride per 100 g of toluene are added, the mixture is maintained at a temperature of 20° to 21° C. under agitation for a period of 30 minutes. Subsequently, 150 ml of an aqueous 5 N sodium hydroxide solution are added very slowly, the temperature is maintained at 20° to 25° C. under agitation for a period of 15 minutes. The mixture is then evaporated under vacuum, whereby the outside temperature is below 45° C., and the constant volume of the reaction medium is maintained by adding demineralized water (1 liter). Then the mixture is cooled to a temperature of 18°-20° C., agitated for a further period of 30 minutes, and centrifuged. After washing the residue with water and drying it, 78.5 g of the mixture of the two epimers A and B of the (±)14,15-dihydro-(3β,16α)-20,21-dinoreburnamenine-14-ol are obtained.

NMR-spectrum (in deuteropyridine)

absorption at about 6.26 ppm: hydrogen in the 14-position, this band corresponds to the isomer A absorption at about 5.76 ppm: hydrogen in the 14-position, this band corresponds to the isomer B.

STAGE B Isomer A of the (±)14,15-dihydro-(3β,16α)-20,21-dinoreburnamenine-14-ol 78.4 g of the product which is obtained in the above Stage A are mixed with 784 ml of methanol and 784 ml of a 5 N sodium hydroxide solution, the mixture is heated to a temperature of from 70° to 75° C. during a period of two hours, then is cooled to a temperature of 10°-22° C., and 785 ml of methanol and 2350 ml of methylene chloride are added. The aqueous phase is separated and re-extracted with 300 ml of methylene chloride. The organic solution is dried, filtered, evaporated to dryness and mixed with methanol. The resulting paste is centrifuged and washed with water. 67.9 g of the final product are obtained.

PHYSICAL DATA OF THE PRODUCT

Melting point: 255° C.

Elementary analysis: $C_{17}H_{20}ON_2$ calculated 76.08% C, 7.51% H, 10.44% N. found 76.3% C, 7.4% H, 10.2% N.

NMR-spectrum (in deuteropyridine)

absorption at about 6.26 ppm: hydrogen in the 14-position.

EXAMPLE 4: Isomer B of the (±)14,15-dihydro-(3β,16α)-20,21-dinoreburnamenine-14-ol 10 g of (±)(3β,16α)-20,21-dinoreburnamenine-14(15H)one hydrochloride are dissolved in 100 ml of toluene under inert gaz atmosphere. 20 ml of solution containing 25 g of sodium aluminum diethyl hydride per 100 g of toluene are added within a period of 15 minutes at a temperature of 20° C. The mixture is maintained at a temperature of 20° C. for a period of 30 minutes and is then poured into 1 liter of ice-water, agitated for 10 minutes and centrifuged. The filtered off residue is mixed with methylene chloride and the resulting solution is centrifuged and the organic phase is washed with water, dried, and evaporated to dryness. The residue is crystallized from ether and 1.6 g of the final product are obtained.

PHYSICAL DATA OF THE PRODUCT

Melting point: 235° C.

Elementary analysis: $C_{17}H_{20}ON_2$ calculated 76.08% C, 7.51% H, 10.44% N. found 76.2% C, 7.7% H, 10.3% N.

NMR-spectrum (in deuteropyridine)

absorption at about 5.76 ppm: hydrogen in the 14-position

EXAMPLE 5: Pharmaceutical formulations (a) tablets tablets of the following composition are prepared by mixing the various ingredients and tabletting the mixture in a conventional tabletting procedure:

Isomer A of the $(\pm)$14,15-dihydro-($3\alpha,16\alpha$)-20,21-dinoreburnamenine-14-ol ... 30 mg carrier material ... q.s. for a tablet. (The carrier material contains lactose, wheat starch, pretreated starch, rice starch, magnesium stearate, and talcum).

(b) capsules capsules of the following composition are prepared by mixing the various ingredients and filling the mixture into capsules:

Isomer A of the $(\pm)$14,15-dihydro-($3\beta,16\alpha$)-20,21-dinoreburnamenine-14-ol ... 30 mg carrier material ... q.s. ad 350 mg (The carrier material contains talcum, magnesium stearate, and highly dispersed silicic acid).

Pharmacological tests (1) Determination of the acute toxicity

The acute toxicity is determined in groups of 10 male and female mice having a weight of 20–22 g which have been fasting since the evening before. A solution of the compound in a physiological serum to which a few drops of hydrochloric acid have been added (the test compound thus is in a hydrochloride solution) is administered intravenously. The lethality is recorded daily during 1 week. The 50% lethal dose ($LD_{50}$) is calculated according to the method of J. T. Lichfield and F. Wilcoxon (J. Pharm. Exp. Therap. 96, 99 (1947). The results are given in table I below.

TABLE I

| Compound of | DL 50 mg/kg I.V. | |
|---|---|---|
| example | male mice | female mice |
| 2 | 70 | 64 |

(2) Determination of the cerebral blood flow rate:

Thermo-flow-indication-test. The test is effected according to the thermo-flow-determination method which is described by Casella et al in Arch. di Fisiologia 1959, 59, 182, and is modified by Ludwigs (Pflüger's Arch. 1954, 259, 35). This method is based on the determination of the variation of the thermo-conductability of the tissue, the latter is related to the variation in the blood flow. The thermal conductability is determined by means of a thermistor which is conveniently placed into the cranial cavity below the dura mater. The tests have been effected on a group of cats which have been anesthetized by intravenously administering a chloralose-methane mixture. Furthermore the arterial pressure of the animals is determined by means of an electronic transductor. The results are given in Table II below.

TABLE II

| Compound | DOSE (mg/kg) I.V. | Effects on the cerebral blood flow and the arterial pressure |
|---|---|---|
| Compound of example 2 | 2,5 mg/kg | Marked increase of the cerebral blood flow within 10 minutes accompanied by a slight decrease of the arterial pressure |
| | 0,5 mg/kg | Slight increase of the cerebral blood flow accompanied by a slight hypertension |
| | 0,1 mg/kg | Slight increase of the cerebral blood flow without alteration of the arterial pressure level |
| Vincamine | 1 mg/kg | Medium and inconstant increase of the cerebral blood flow accompanied by a slight hypotension. |

3. Effect on the vertebral and the femoral blood flow of the dog

The tests are effected on the opened thorax of male and female Beagle dogs which have a weight of 10 to 13 kg and have been anesthetized by means of chloralose. The vertebral blood flow (expressed in ml/minute) is measured by means of an electromagnetic pressure-flowmeter "Statham" which is placed at the beginning of the right vertebral artery. The femoral blood flow is determined under the same conditions at the level of the right femoral artery. Furthermore the arterial blood pressure and the cardiac frequency are recorded. The various parameters are determined before and after the injection of the test compound and the maximum differences have been calculated and are expressed as percent. The results are given in the table III below, wherein n represents the number of experiments which have been carried out for each dose of the test compound.

CONCLUSION

Starting at the dose of 0.1 mg/kg i.v., the compound of example 2 leads to an increase of the vertebral blood flow, without provoking any markable alteration of the arterial blood pressure or the cardiac frequency. Furthermore it leads to an increase of the femoral blood flow.

At the same dosages, vincamine irregularly alters the femoral and the vertebral blood flow (as can be seen from the range of deviations from the average value of the data in table III) and provokes a slight decrease of the cardiac frequency.

TABLE III

| Compound | Doses (mg/kg) | Variation: | | | | | | | |
|---|---|---|---|---|---|---|---|---|---|
| | | Average Arterial Pressure | n | Cardiac Frequency | n | Vertebral Blood Flow | n | Femoral Blood Flow | n |
| Compound of Example 2 | 0.1 | $-0.2 \pm 2.8$ | 4 | $8.2 \pm 3.5$ | 4 | $15.2 \pm 14$ | 4 | $93.3 \pm 6.7$ | 3 |
| | 0.3 | $4.7 \pm 1.1$ | 12 | $8 \pm 3.0$ | 12 | $27.2 \pm 11.9$ | 10 | $44.7 \pm 13.2$ | 8 |
| Vincamine | 0.1 | $-6.5 \pm 6.5$ | 2 | $-10 \pm 10$ | 2 | $5 \pm 5$ | 2 | 17 | 1 |
| | 0.3 | $-0.6 \pm 1.4$ | 5 | $-15.2 \pm 4.3$ | 5 | $1.0 \pm 11.5$ | 5 | $-2.8 \pm 2.8$ | 4 |

What is claimed is:

1. A compound selected from the group consisting of compounds having the formula I

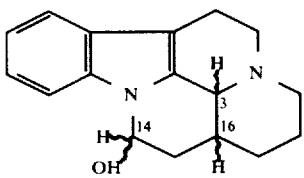

wherein the hydroxyl in the 14-position of the molecule is in either of the two possible positions at the carbon atom in the 14-position and the hydrogens in the 3-position and the 16-position of the molecule are in cis- or in trans-position to each other, racemates and mixtures thereof or a pharmaceutically-acceptable acid addition salt thereof.

2. The compound as defined in claim 1 wherein the hydrogens in the 3-position and the 16-position of the molecule are in transposition to each other.

3. The compound as defined in claim 1 wherein the hydrogens in the 3-position and the 16-position of the molecule are in cis-position to each other.

4. The compound as defined in claim 1 which is the isomer A of (±)14,15-dihydro-(3α,16α)-20,21-dinoreburnamenine-14-ol or a pharmacologically-acceptable acid addition salt thereof.

5. The compound as defined in claim 1 which is the isomer A of (±)14,15-dihydro-(3β,16α)-20,21-dinoreburnamenine-14-ol or a pharmacologically-acceptable acid addition salt thereof.

6. The compound as defined in claim 1 which is the isomer B of (±)14,15-dihydro-(3β,16α)-20,21-dinoreburnamenine-14-ol or a pharmacologically-acceptable acid addition salt thereof.

7. A cerebral vasodilating composition comprising an effective vasodilating amount of a compound as defined in claim 1 and a pharmaceutically acceptable inert diluent.

8. A cerebral vasodilating composition comprising an effective vasodilating amount of a compound as defined in claim 2 and a pharmaceutically acceptable inert diluent.

9. A cerebral vasodilating composition comprising an effective amount of a compound as defined in claim 3 and a pharmaceutically acceptable inert diluent.

10. A cerebral vasodilating composition comprising an effective amount of a compound as defined in claim 4 and a pharmaceutically acceptable inert diluent.

11. A cerebral vasodilating composition comprising an effective amount of a compound as defined in claim 5 and a pharmaceutically acceptable inert diluent.

12. A cerebral vasodilating composition comprising an effective amount of a compound as defined in claim 6 and a pharmaceutically acceptable inert diluent.

13. A method of treatment of cerebral vascular disorders and cerebral syndroms provoked by an alteration of the cerebral vascular circulation which comprises the step of administering to a human being in need of such treatment an effective vasodilating amount of a compound as defined in claim 1.

14. A method of treatment of cerebral vascular disorders and cerebral syndroms provoked by an alteration of the cerebral vascular circulation which comprises the step of administering to a human being in need of such treatment an effective vasodilating amount of a compound as defined in claim 4.

15. A method of treatment of cerebral vascular disorders and cerebral syndroms provoked by an alteration of the cerebral vascular circulation which comprises the step of administering to a human being in need of such treatment an effective vasodilating amount of a compound as defined in claim 5.

16. A method of treatment of cerebral vascular disorders and cerebral syndroms provoked by an alteration of the cerebral vascular circulation which comprises the step of administering to a human being in need of such treatment an effective vasodilating amount of a compound as defined in claim 6.

* * * * *